United States Patent
DeMarco

(10) Patent No.: US 9,194,848 B2
(45) Date of Patent: Nov. 24, 2015

(54) MULTI-MEASUREMENT FLOW CELL ASSEMBLY FOR LIQUID CHROMATOGRAPHY

(71) Applicant: Nicholas DeMarco, Raleigh, NC (US)

(72) Inventor: Nicholas DeMarco, Raleigh, NC (US)

(73) Assignee: Practichem, LLC, Morrisville, NC (US)

( * ) Notice: Subject to any disclaimer, the term of this patent is extended or adjusted under 35 U.S.C. 154(b) by 129 days.

(21) Appl. No.: 14/120,425

(22) Filed: Mar. 14, 2014

(65) Prior Publication Data

US 2015/0260693 A1 Sep. 17, 2015

Related U.S. Application Data

(60) Provisional application No. 61/794,081, filed on Mar. 15, 2013, provisional application No. 61/824,219, filed on May 16, 2013.

(51) Int. Cl.
*G01N 21/00* (2006.01)
*G01N 30/26* (2006.01)
(Continued)

(52) U.S. Cl.
CPC ............... *G01N 30/26* (2013.01); *G01N 30/64* (2013.01); *G01N 30/74* (2013.01); *H05B 33/0845* (2013.01); *G01N 2030/645* (2013.01)

(58) Field of Classification Search
CPC ... H01J 37/32935; G01N 21/64; G01N 21/68; G01N 2015/1037; G01J 3/02
USPC ..................................... 356/72–72, 300–445
See application file for complete search history.

(56) References Cited

U.S. PATENT DOCUMENTS 4,462,962 A 7/1984 Baba et al.
6,307,204 B1 10/2001 Kanomata et al.
(Continued)

FOREIGN PATENT DOCUMENTS

EP 0335268 A2 10/1989
EP 1522849 A1 4/2005

OTHER PUBLICATIONS

Keithly Instruments, Inc., "Measuring the Resistivity and Determining the Conductivity Type of Semiconductor Materials Using a Four-Point Collinear Probe and the Model 6221 DC and AC Current Source", "Keithly Application Note Series", 2005, pp. 1-4, No. 2615.
(Continued)

*Primary Examiner* — Abdullahi Nur
(74) *Attorney, Agent, or Firm* — Hultquist IP; Steven J. Hultquist

(57) ABSTRACT

A detector for detecting constituents of a liquid for use in liquid chromatography is disclosed. The detector includes a first optical flow cell body and a second optical flow cell body, each having a channel therethrough that allows passage of a liquid from an inlet port to an outlet port. The first and second optical flow cell bodies are arranged in series such that the liquid exiting the outlet port of the first optical flow cell body enters the inlet port of the second optical flow cell body. An insulator resides between the first optical flow cell body and the second optical flow cell body, which is adapted to electrically insulate the first optical flow cell body from the second optical flow cell body while allowing the liquid to pass from the first optical flow cell body to the second optical flow cell body. The first optical flow cell body is adapted to facilitate measurement of absorption by the liquid of a first wavelength of light, and second optical flow cell body is adapted to facilitate measurement of absorption by the liquid of a second wavelength of light. The first and second optical flow cell bodies are further adapted to perform as electrodes for measuring the conductivity of the liquid.

25 Claims, 5 Drawing Sheets

(51) Int. Cl.
*G01N 30/74* (2006.01)
*G01N 30/64* (2006.01)
*H05B 33/08* (2006.01)

(56) References Cited

U.S. PATENT DOCUMENTS

| | | | |
|---|---|---|---|
| 6,391,541 | B1 | 5/2002 | Petersen et al. |
| 2002/0092340 | A1* | 7/2002 | Prater ............... G02B 7/1821 73/24.02 |
| 2004/0188333 | A1 | 9/2004 | Allington et al. |
| 2005/0011836 | A1 | 1/2005 | Bidlingmeyer et al. |
| 2005/0213088 | A1 | 9/2005 | Brewer et al. |
| 2006/0132770 | A1 | 6/2006 | Girvin et al. |
| 2007/0103681 | A1 | 5/2007 | Hull et al. |
| 2008/0246954 | A1 | 10/2008 | Kitaoka et al. |
| 2008/0252884 | A1 | 10/2008 | Carr |
| 2009/0116011 | A1 | 5/2009 | Kenyon |
| 2010/0165325 | A1 | 7/2010 | Tabata |
| 2010/0230353 | A1 | 9/2010 | Kerr et al. |
| 2011/0141465 | A1 | 6/2011 | Jeannotte et al. |
| 2011/0228271 | A1 | 9/2011 | Vacca et al. |
| 2012/0009667 | A1 | 1/2012 | Peterson et al. |
| 2012/0193555 | A1 | 8/2012 | Steel et al. |

OTHER PUBLICATIONS

Radiometer Analytical SAS, "CDM230 Conductivity Meter", 2002, pp. 1-2, Published in: Villeurbanne Cedex, France.
Note: For the non-patent literature citations that no month of publication is indicted, the year of publication is more than 1 year prior to the effective filing date of the present application.

* cited by examiner

MULTI-MEASUREMENT FLOW CELL ASSEMBLY FOR LIQUID CHROMATOGRAPHY

CROSS-REFERENCE TO RELATED APPLICATIONS

This application claims priority of U.S. Provisional Patent Application No. 61/794,081 filed Mar. 15, 2013 and U.S. Provisional Patent Application No. 61/824,219 filed May 16, 2013. The disclosures of all such applications are hereby incorporated herein by reference in their respective entireties, for all purposes.

BACKGROUND

Detectors, such as UV absorbance detectors, are measuring instruments used in liquid chromatography to detect and/or measure constituents of a liquid solution. A flow cell comprises part of a detector and defines the sensor volume of the detector. The flow cell's internal cavity, through which the liquid specimen flows, exposes properties of the liquid to measuring apparatus.

Optical Absorbance

An optical flow cell allows transmission of ultraviolet or visible light through liquid flowing therein. The liquid's absorbance can be measured for the purpose of detecting the presence, and determining the concentration, of certain chemical compounds, such as species of protein, DNA or small drug molecules. Absorbance is calculated using Beer-Lambert's law:

$$A = \epsilon bc \tag{1}$$

Where A is absorbance (unitless);
$\epsilon$ is molar absorbtivity of the analyte (L mol$^{-1}$ cm$^{-1}$)
b is optical path length (cm);
c is concentration (mol L$^{-1}$).
Also, $$A = \log_{10}\left(\frac{P_0}{P}\right) \tag{2}$$

Where P0 is the incident radiant flux;
P is the transmitted radiant flux.

The Optical Flow Cell

The optical flow cell is typically defined by a bore in the interior of a body, comprising a fluid inlet and fluid outlet and establishing the flow path for liquid wherein absorbance is measured. The optical flow cell body typically includes a second bore, defining an optical path which allows light to pass through at least a portion of the liquid flow path. A portion of the liquid flow path is shared with the optical path and usually runs parallel to the optical path. Windows, with the aid of a sealing gasket, seal against the ends of the second bore, allowing light to pass while retaining the liquid inside the optical flow cell body. The windows are often made from fused silica or another material optically transparent at the measured wavelengths, compatible with the liquid and sufficiently strong to withstand the internal flow cell cavity forces. Typically, the detector body includes one or more grooves or slots on each end of the optical path where the optical path end face joins a window. The groove directs fluid into one open end of the optical path and out the opposing end. This combination of geometric features promotes liquid flow through the entire optical path and minimizes mixing of the currently passing liquid with liquid that had flowed through the cavity earlier. Typically, a window sealing gasket made from a compliant material compatible with the liquid, like PTFE (DuPont Teflon®) or an elastomeric material like perfluoroelastomer (DuPont Kalrez®), silicone or rubber (Buna-N) is disposed between the window and the cell body as a seal, retaining the liquid in the flow cell.

Multi Wavelength Detection

In liquid chromatography systems, it is often necessary or desirable to measure the liquid solution's absorption at more than one optical wavelength. Light absorption detectors often employ a broad spectrum light source coupled to a monochromator to select each wavelength of interest. Other light absorption detectors use a broad spectrum lamp and a holographic grating to split the transmitted light into constituent wavelengths, then measure the transmitted wavelengths with a linear array of light sensitive elements such as photodiodes or charge-coupled devices (CCDs).

Conductivity

Electrolytic conductivity of a liquid solution is often related to the ionic concentration of a solution. Measured in conjunction with light absorbance, conductivity provides additional information about the liquid, such as salt concentration and protein concentration. Conductivity is usually determined by measuring the resistance across two electrodes. Dilute solutions, typical of liquid chromatography, follow Kohlrauch's law:

$$\Lambda_m^\infty = v_{cation}\lambda_{cation}^\infty + V_{anion}\lambda_{cation}^\infty \tag{3}$$

Where $\Lambda^\infty_m$ is the molar conductivity of an electrolyte;
$V_{cation}$ and $V_{anion}$ are the numbers of cations and anions per formula unit respectively;
$\Lambda^\infty_{cation}$ and $\lambda^\infty_{cation}$ are the molar conductivities of the cation and anion at infinite dilution respectively.

Conductivity Flow Cell

Typical conductivity flow cells include two metal disks including holes in their centers through which the liquid solution flows. The metal disks are separated by an insulator, preventing electrical conduction between the optical flow cell bodies other than through the liquid solution. Thereby, the disks act as electrodes for measuring the conductivity of the liquid.

In some cases, there is a substantial amount of current flow, not due to the liquid's conductance, present in the measured signal. These erroneous currents are due to inherent properties of the electrodes, like capacitance and fringe effects.

Two conductive surfaces separated by an insulator form a capacitor. The two conductivity electrodes meet this definition and, therefore, form a capacitor. The capacitance of the conductivity electrodes affects the conductivity readings.

Some electrical current flows through the longest path through the fluid. Other current flows through the shortest path. These variations in path length cause fringe effects, a broadening of the conductivity reading.

Pairing Optical and Conductivity Flow Cells

Conventional liquid chromatography systems contain separate flow cells for measuring optical absorbance and for measuring electrolytic conductivity. Furthermore, said systems may contain several flow cells in series, each measuring a single property of a liquid specimen solution. It would be desirable to reduce the number of flow cells in a liquid chromatography system for several reasons. Flow cells take up space in compact liquid chromatography systems. Flow cells add to the length and complexity of the liquid flow path. Multiple flow cells connected in series adds to the number of liquid connection points, increasing the likelihood for liquid leaks or obstructions to smooth liquid flow. Moreover, flow cells naturally increase liquid solution turbulence, causing errors in absorbance and conductivity measurement. Most importantly, the internal volume of these flow cells and their interconnections form volumes for previously separated compounds to remix, reversing the effects of the chromatographic separation process.

The Combined Sensor

Accordingly, it would be desirable to provide a flow cell that can perform measure the physical properties of the liquid solution and substantially overcome the disadvantages and problems encountered by employing multiple separate flow cells. The present invention provides such flow cells, methods for their use, and liquid chromatography systems including such flow cells.

SUMMARY OF THE INVENTION

In one embodiment of the invention, a flow cell system is described. The flow cell system includes first and second optical flow cell bodies, each of which includes an inlet port, an outlet port, and a fluid passage through the optical flow cell body connecting the inlet port to the outlet port.

In one embodiment, a housing supports the first optical flow cell body and the second optical flow cell body, such that the first and second optical flow cell bodies are in series, with the outlet port of the first optical flow cell body adjacent to the inlet port of the second optical flow cell body. In another embodiment, the flow cells are stackable, that is, connected fluidically in series, each with its own housing.

A first conductive material is adjacent to the outlet port of the first optical flow cell body, positioned such that would be in contact with any fluid passing through the flow cell, a second conductive material is adjacent to the inlet port of the second optical flow cell body, positioned such that would be in contact with any fluid passing through the flow cell, and an insulator between the first and second conductive materials.

The optical flow cell body can be formed from a conductive material. Alternately, the conductive materials can be physically pressed against the flow cell bodies, or they can be attached to the optical flow cell bodies, mechanically or chemically. As an example of mechanical bonding, a female part at the outlet port of the first optical flow cell body or the inlet port of the second optical flow cell body can be adapted to receive a male part of a conductive material, so that the two are physically mated. As an example of a chemical bonding, the conductive material can be adhered to one or both of the optical flow cell bodies, such as by an epoxy resin or other suitable adhesive that resists degradation under the conditions of use, namely, high pressure, organic solvents, and the like.

The simplest conductive materials are washers, including metallic washers or washers made of or covered by conductive substances (such as conductive polymers or coatings or platings). To provide a better connection between the optical flow cell bodies and the conductive materials, the optical flow cell bodies can include wires, metal plating, and the like. In one aspect of this embodiment, a portion of the flow cell is plated with a metal, such as gold.

The conductivity measuring system can further include an alternating voltage source (AC source). The AC source is connected, directly or indirectly, to the first and second conductive materials, so as to complete a circuit. In one embodiment, the AC source is capable of alternating at more than one frequency.

The presence of the two conductive electrodes with an insulator disposed between them allows one to perform conductivity measurements when a) a liquid solution is passed through the flow cell electrodes and b) the conductive materials are connected to an AC source to drive current through the materials. The liquid solution completes the circuit between the conductive materials, and the current through the circuit changes as the concentration of proteins or other molecules of interest in the liquid solution changes.

Capacitive effects and fringe effects can result in erroneous readings. Both effects can be substantially subtracted using multiple techniques. In one embodiment, the conductivity measurement system comprises more than two conductive material electrodes, such as 3, 4, 5, 6, or more conductive material electrodes, which, when connected to an AC source, function as reference electrodes. In one aspect of this embodiment, where the initial electrodes are formed by the conductive materials at the outlet port of the first optical flow cell body and the inlet port of the second optical flow cell body, an additional two electrodes can be formed by placing conductive materials at the inlet port of the first optical flow cell body, and the outlet port of the second optical flow cell body.

Additional conductivity electrodes beyond two collectively form a reference pair having the same error signal as the measuring electrode pair, but do not measure the liquid conductivity. By subtracting the reference signal, only the conductivity due to liquid conductance remains, effectively subtracting the non-conductivity current effects.

In another embodiment, the AC source operates at varying frequencies depending on the measured value of conductance. By varying the AC source frequency, cell capacitive effects become apparent and separately measurable. These capacitive effects can be subtracted from the measurement to improve measurement accuracy.

In addition to measuring conductivity, the flow cells can be adapted for use in detecting the presence, and determining the concentration, of certain chemical compounds, such as species of protein, DNA or small drug molecules by means of absorbance and/or fluorescence. Accordingly, in one aspect of this embodiment, the first and/or second optical flow cell bodies can include one or more paths through which light can pass, typically in a perpendicular direction to the liquid path between the inlet and outlet ports on the optical flow cell bodies.

The light path through the first and/or second optical flow cell bodies includes a window with an inside and an outside surface. This window is formed of a material that a) transmits light at the wavelength being evaluated, and b) has suitable physical and chemical properties to withstand the conditions of use. Representative materials that can be used to prepare the window(s) include fused silica (quartz), MgF, UV transparent polymers like cyclic olefin copolymers (example Topas® COC). In one embodiment, the window(s) are coated, on one or both surfaces, with an anti-reflective coating to maximize the light transmitted through the window.

Light from one or more suitable light sources can be passed through the window, such that it travels through the flow cell and the liquid whose absorbance is to be measured and on to a photodetector. The absorbance can be computed, and where the eluent includes a protein containing one or more absorbing amino acids, the absorbance will be higher than when no protein is present.

Light can be passed from a single light source through one of the optical flow cell bodies, from multiple sources through one of the optical flow cell bodies, or from multiple sources through multiple optical flow cell bodies.

The light source(s) can be located in the housing, or can be located outside of the housing. Where the light source(s) are located outside of the housing, the light can be transmitted optionally including one or more lens elements into the housing through air, or by means of a fiber optic cable, or other fiber optic element. In this embodiment, the fiber optic element ideally resides, at least in part, within the housing.

The light source(s) must be capable of generating light at a wavelength that is suitable for the molecules being detected. Typically, this light is in the UV or visible range (UV/VIS). Where fluorescence is also being measured, at least one light source must be capable of generating light that stimulates fluorescence in the substance to be detected.

Representative light sources include, but are not limited to, lasers, light emitting diodes (LEDs), such as TOPLEDs (OSRAM Opto Semiconductor), UVTOP® (Sensor Electronic Technologies), or Nichia UV-LEDs (Nichia Corporation, Tokushima, Japan) http://www.nichia.co.jp/en/product/uv-led.html) some of which provide monochromatic light, or nearly monochromatic light, and deuterium, xenon, mercury, zinc, and tungsten lamps, which provide broader spectrum light output.

Where the light is monochromatic light, or nearly monochromatic light, and is of a desired wavelength for the analysis, there is no need to separate or filter the light using a prism, holographic grating or bandpass filter and direct light of a desired wavelength through the optical flow cell body. On the other hand, where the light is not monochromatic, it may be desirable to use a prism or grating or filter to select the desired wavelength or range of wavelengths of light and direct the resulting light through the optical flow cell body. When a prism, grating or filter is used, the transmitted wavelength can be varied, depending on the molecule of interest being eluted from a column and through the flow cell system. For example, light at a wavelength of 280 nm is absorbed by most amino acids and is preferred for measuring protein concentration, and 260 nm is preferred for measuring DNA concentration (see, for example, Sambrook and Russell (2001). Molecular Cloning: A Laboratory Manual (3rd ed.). Cold Spring Harbor Laboratory Press. ISBN 978-0-87969-577-4.

Because the flow cells are relatively small and typically pass relatively small optical powers, the photodetectors used to measure the transmitted light rely on small currents, often measured in the nano Ampere scale. Where there is only a relatively small amount of energy being detected, even tiny levels of background noise cause the signal to noise ratio (S/N) to be detrimental to the measurement. In one embodiment, this effect is minimized by using light with a relatively high intensity. The relatively high light intensity provides significantly more signal to the detector, thus improving S/N. Liquid solutions passing through the flow cell can be negatively affected by high energy UV radiation, which can denature proteins and can precipitate on the flow cell surfaces, artificially increasing the measured absorbance. Accordingly, in one aspect of this embodiment, this limitation is addressed by operating the light source in a high peak power, short duration pulsed mode. Between pulses, the light system cools sufficiently such that the light source lifetime is maintained at or near normal levels and the flow cell windows are not fouled. To measure the dynamically flowing liquid sample with sufficient resolution, the light source is pulsed rapidly. For example, the pulse intervals may be between 0.1 and 500 milliseconds. Within each pulse, the light source will be on less than about 50% of the complete cycle, preferably less than about 25% of the cycle, and still more preferably, less than about 10% of the cycle. For example, one can have a 76 microsecond light pulse within a one millisecond cycle. Pulse cycles shorter than about 0.1 milliseconds become difficult to control, resulting in signal ringing and timing inaccuracies. The light pulse should not exceed around 50% of the cycle time for sufficient thermal recovery between pulses. The frequency of the pulses, and the length of the cycle, can be adjusted using appropriate hardware and software controls.

In one embodiment, each light source package includes more than one LED device, where each LED can be independently enabled. In this embodiment, a first light pulse from one LED can be passed through the flow cell, followed by a second light pulse through the same flow cell. Both LEDs can be of the same wavelength or different wavelengths to confirm the value of the other LED or to return additional property data on the liquid samples under measurement.

As discussed above, it is important that the light beams pass in a path substantially perpendicular to the optical bore through the flow cell. A single light emitting device package containing more than one light LED source element within it can be used, where the light sources are substantially close to each other, such that each light source reaches the window substantially co-axially. As the light source deviates from the axis through the optical bore (said axis is also substantially normal to the windows), greater percentages of the incident light are reflected away from the photodetector. For example, the individual light source elements can be offset from the flow cell optical axis by as much as 5° and still deliver sufficient light to the photodetector for measurement. The use of one conduit (in this embodiment, the optical bore) to transmit multiple wavelengths at different times is analogous to the technique known to those of skill in the art of signal transmission as time division multiplexing. In time division multiplexing, two or more signals are interleaved in time through the same channel, thereby minimizing the number of channels required. Similarly to telephone lines, additional flow cells are expensive and should be minimized.

When the light is pulsed, it is also possible to minimize noise, improving the signal to noise ratio by synchronously gating the photodetector, so the amplifier accumulates signal in approximately the same time frame as the source light is active. Photodiodes and other photodetectors generate some electricity regardless of light falling on their active surfaces. This electricity is commonly known as "dark current" because the current flows even if the sensor's surface is dark. Accordingly, in one embodiment, the photodetector is pulsed to convert light intensity to an output current that mirrors the pulsing of the light source. In one aspect of this embodiment, the photodetector includes an amplifier, and the pulsing of the photodetector is accomplished by synchronously gating the amplifier.

In some embodiments, it may be desired to focus the light beams so that they pass through the flow cell window. In these embodiments, the system can include one or more lenses, filters, and/or apertures, positioned such that the lenses, filters, and/or apertures are in the path of the light emitted from one or more of the light sources, before and/or after the light passes through the first or second optical flow cell body. Representative lenses include concave, convex, plano-concave, plano-convex, ball, hemispherical, collimating, and Fresnel lenses.

In addition to including the windows through which light can pass, and conductive materials that can serve as electrodes when a current is applied, it is also important, for example, to be able to use information regarding the absorbance, fluorescence, or conductivity to determine when a molecule of interest has eluted from a column.

Accordingly, the flow cell systems can be connected to, or comprise, one or more detectors. Where light is being passed through the optical portion of the optical flow cell bodies, and determination of absorbance or fluorescence is desired, the detector is ideally a photodetector, such as a silicon photodiode, charge-coupled device (CCD), photoelectron multiplier. In one embodiment, the photodetector is external to the housing, but light is transmitted to the detector via a fiber optic element that resides, at least in part, within the housing. Where conductivity is to be measured, the flow cell systems are ideally connected to, or comprise, a conductivity detector.

Because conductance, fluorescence, and the like can vary depending on the temperature of the liquid solution, it can be important to have the ability to measure the temperature. Accordingly, in some embodiments, the flow cell system, particularly the housing portion of the system, includes a temperature measuring device, such as a thermocouple or resistive temperature device (often called RTD, or Pt100), although any device.

In another embodiment, the invention relates to an overall liquid chromatography system that includes the flow cell systems described herein. In this embodiment, the complete liquid chromatography system typically includes one or more mobile phases, which are typically stored in one or more reservoirs, and a pump for moving the mobile phase(s). Where mobile phases are to be mixed, for example, when used in gradient elution, the system typically also includes one or more valves. The chromatography system also includes one or more chromatography columns, each of which include a suitable column packing material. Samples are injected onto the column(s) through a sample injection port. As the eluent (in this case, the mobile phase(s) passes through the end of the column, it can then pass through the flow cell systems described herein.

In a further embodiment, the conductivity portion of the detector system described herein can be used in a chromatography system to verify the mobile phase components have been attached to the proper fluid inlets and the control system has been configured to deliver the correct ratio of mobile phase components. Within many chromatography techniques, for example in biochromatography, one mobile phase component contains a substantially lower salt concentration than other mobile phase components. A transposition of this low salt component becomes apparent rapidly after the commencement of the chromatography process.

In a further embodiment, the conductivity portion of the detector, the absorbance portion of the detector or both the conductivity portion and the absorbance portion in concert can be used to determine the completion of a chromatographic step. Certain steps such as equilibration, sample load, wash and regenerate are considered complete when the passage of additional mobile phase through the system results in effectively no additional chromatographic change. The chromatographic change tends to correlate with changes in absorbance, conductivity or both absorbance and conductivity. Monitoring absorbance and conductivity during these steps and further monitoring the rate of change of these parameters often indicates completion of the step.

In a further embodiment, the invention relates to a method for detecting the presence or absence of protein, DNA, or another molecule of interest in an eluent by measuring the conductivity of the eluent. The method involves passing a mobile phase through a liquid chromatography column comprising the flow cell systems described above. The conductivity of the mobile phase as it elutes from the column (i.e., the eluent), and as it passes through the flow cell system, can be determined, and this can be used to define baseline conductivity. A sample that comprises one or more molecules of interest, such as proteins or DNA, can then be injected onto the liquid chromatography column. A chromatographic separation is performed by pumping the eluent through the liquid chromatography column. Periodic or continuous measurements of the conductivity of the eluent can be taken as the eluent passes through the optical flow cell bodies. An increase in conductance relative to the baseline conductance is indicative of the presence of a molecule of interest in the eluent.

In a still further embodiment, the invention relates to a method for detecting the presence or absence of a protein, DNA, or other molecule of interest in an eluent, by measuring the absorbance or fluorescence of the eluent. The method involves passing a mobile phase eluent through a liquid chromatography column comprising a flow cell system as described herein, to form an eluent.

A beam of light, at a wavelength suitable for detecting the presence of the molecule of interest in the eluent, is passed through the first and/or second optical flow cell body of the flow cell system in a direction substantially perpendicular to the direction in which the eluent flows through the optical flow cell bodies. The light is then passed through the optical flow cell bodies to a photodetector, and an initial light intensity is measured.

A sample which includes one or more molecules of interest is then injected onto the liquid chromatography column. Chromatographic separation is performed by pumping the mobile phase through the chromatography column to form an eluent. The intensity of light passed through the flow cell optical paths and directed to a photodetector can be measured, either periodically or continuously, and the light intensity can be compared to the initial light intensity. A decrease in light intensity measured by the photodetector, relative to the initial light intensity, is indicative of a protein or other compound of interest's presence in the eluent.

In one embodiment, light is measured in each of the two flow cells at different wavelengths. For example, where the wavelengths are set at 260 nm and 280 nm, one can measure protein and DNA concentrations. In another embodiment, light is measured in each of the two flow cells at the same wavelength. This can help determine whether there are any distortions caused by artifacts in one of the flow cells, because in the absence of such artifacts, assuming the same light intensity, flow cell size, and flow cell composition, the two signals should be identical. In a third embodiment, in addition to having two light sources at the same light intensity, one in each flow cell, one can further have two (or more) light sources in one or both of the flow cells. Particularly where the light is pulsed, as described above, the system can provide pulses of light at a first wavelength in the cycle, and pulses of light at a second wavelength either within the same cycle, or in a separate cycle. It is generally preferred to allow sufficient time between pulses of light of different frequencies, so as to avoid interference by the light beams.

As fluid flows through the first flow cell, the insulator, and the second flow cell, conductivity can be measured. Conductivity of that specimen fluid is measured by connecting the cell bodies, or, more specifically, connecting the conductive material present on both sides of the insulator, to a power supply and applying an AC current thereto. The variation in the electrical resistance of the specimen liquid can be measured, either continuously, or at desired times during a chromatographic run. In one embodiment, the conductivity is also measured in a pulsed manner rather than in a continuous manner. In one aspect of this embodiment, the pulses by which conductivity is measured are timed to avoid overlapping with the light pulses, so that noise and other artifacts caused by the light signal, and detection thereof, are not inadvertently captured as part of the conductivity measurement or vice versa.

Using the flow cell systems described herein, the absorbance at two distinct wavelengths and the conductivity of the eluent, can all be measured essentially simultaneously within the same flow cell system. Thus, this flow cell system eliminates the need for a separate conductivity measuring device and adds an additional absorbance measurement at a different wavelength into a single, compact housing. This compact, single-device design reduces the space that is otherwise occupied by the use of multiple, separate flow cell assemblies. It also reduces the potential for measurement error which can be introduced by the use of a series of multiple separate flow cells. This device further reduces the system's non-chromatographic fluidic volume, reducing post-separation remixing of the eluent.

The present invention will be better understood with reference to the following detailed description.

DETAILED DESCRIPTION

Figure 1:
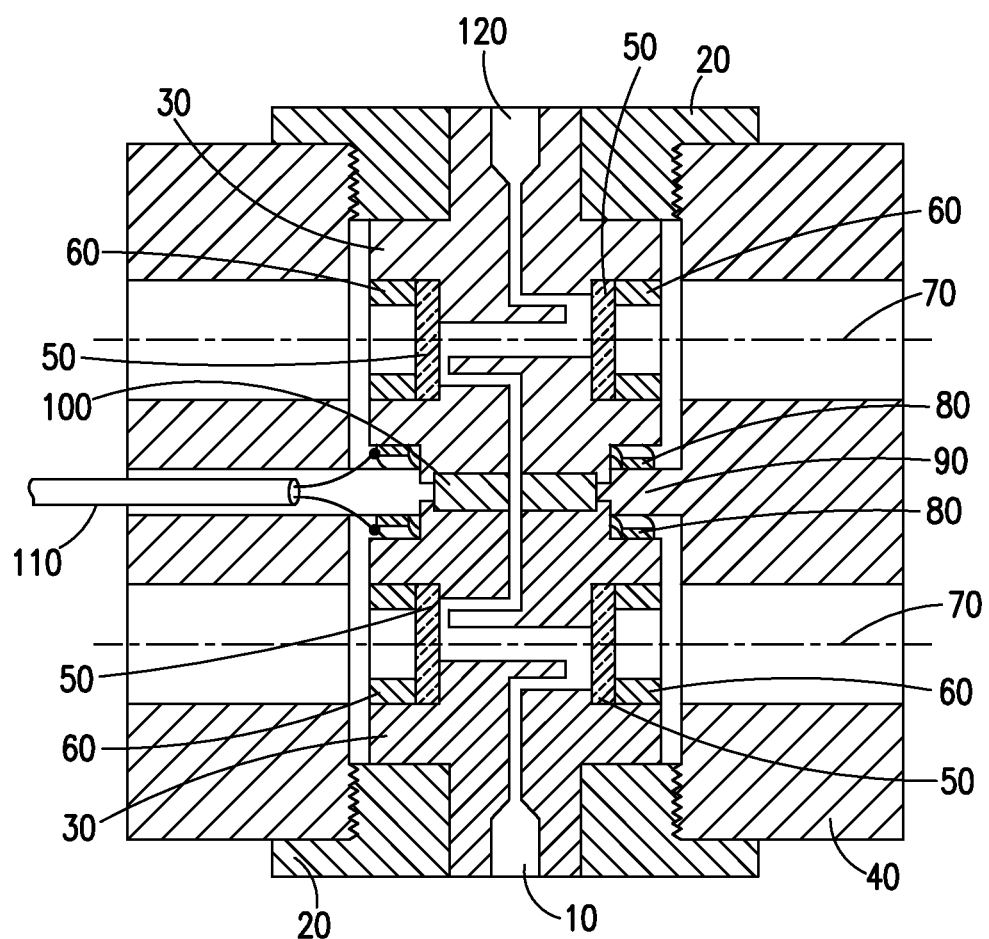
FIG. 1 shows a sectional view of an embodiment of a multi-measurement flow cell assembly.

Flow cell assemblies comprising first and second optical flow cell bodies, each of which includes an inlet port, an outlet port, and a fluid passage through the optical flow cell body connecting the inlet port to the outlet port, are disclosed. HPLC devices including the flow cell assemblies are also disclosed, as well as methods for using the flow cell assemblies.

In one embodiment, a housing supports the first optical flow cell body and the second optical flow cell body, such that the first and second flow cell bodies are in series, with the outlet port of the first flow cell body adjacent to the inlet port of the second flow cell body. In another embodiment, the flow cells are stackable in series, each with its own housing.

A first conductive material is adjacent to the outlet port of the first optical flow cell body, positioned such that would be in contact with any fluid passing through the flow cell, a second conductive material is adjacent to the inlet port of the second optical flow cell body, positioned such that would be in contact with any fluid passing through the flow cell, and an insulator between the first and second conductive materials.

The flow cell assemblies allow one to reduce the number of flow cells in a liquid chromatography system. This is advantageous for several reasons. Flow cells take up space in compact liquid chromatography systems and add to the length and complexity of the flow path for the specimen solution. Further, the use of multiple flow cells adds to the number of connection points, which increases the opportunity for leaks or other failures to seal. Moreover, flow cells often increase the amount of turbulence created in the specimen solution, which can cause inaccuracies in and distortion of the conductivity and absorbance measurements. Most importantly, the additional "deal volume" created by the addition of multiple flow cells presents opportunities for previously separated compounds to remix, reversing the effects of the separation process.

Thus, in one embodiment, the invention relates to a flow cell that can substantially overcome the disadvantages and problems encountered by using multiple flow cells.

The disclosed flow cell assembly allows for three or more property measurements to be made in a single, compact device. Conductance and the absorbance at two, three, or more distinct wavelengths, or, alternatively, duplicate absorbance measurements at a single wavelength, can all be measured simultaneously within the same detector. Further, temperature can be measured as well.

Accordingly, in this embodiment, the flow cell assemblies eliminate the need for a separate conductivity measuring device and add, at least, an additional absorbance measurement at a different wavelength, or a duplicate measurement at the same wavelength, into a single, compact housing. The compact, single-device design reduces the space that is otherwise occupied by multiple, separate flow cell assemblies. It also reduces the potential for measurement error which can be introduced by using a series of multiple separate flow cells. Other principal features and advantages of the invention will become apparent to those skilled in the art upon review of the drawings, the detailed description, and the appended claim(s).

The system and its individual components are described in detail below.

I. Flow Cell System

The flow cell systems described herein include two or more flow cells, either within the same housing, or in separate housings. The flow cells have components that enable the measurement of conductivity and/or temperature as fluids pass through the flow cells. The flow cells include inlet and outlet ports, which enable them to be part of a complete chromatography system.

The flow cells can be part of a complete chromatography system which includes at least one reservoir including a mobile phase, a column packed with a stationary phase, a pump to pass the mobile phase through the column, an injection port to introduce a sample to be separated.

The flow cells described herein generally have an optical path diameter between about 1 and about 5 mm, and an optical path length of between about 0.1 and 20 mm.

In addition to measuring conductivity, the flow cells can be adapted for use in detecting the presence, and determining the concentration, of certain chemical compounds, such as species of protein, DNA or small drug molecules by means of absorbance and/or fluorescence. Accordingly, in one aspect of this embodiment, the first and/or second optical flow cell bodies can include one or more paths through which light can pass, typically in a perpendicular direction to the liquid path between the inlet and outlet ports on the flow cell bodies.

The light path through the first and/or second flow cell bodies includes a window with an inside and an outside surface. This window is formed of a material that a) transmits light at the wavelength being evaluated, and b) has suitable physical and chemical properties to withstand the conditions of use. Representative materials that can be used to prepare the window(s) include fused silica (quartz), MgF, UV transparent polymers like cyclic olefin copolymers (example Topas® COC). In one embodiment, the window(s) are coated, on one or both surfaces, with an anti-reflective coating to maximize the light transmitted through the window.

The materials used to prepare the flow cells are, ideally, corrosion resistant, able to withstand the physical conditions of the system (i.e. pressure and forces) and preferably do not bind to proteins. Titanium, specifically Ti 6Al-4V, is an example of one such material. Other alloys composed primarily of titanium (often referred to as Grades 1 through approximately 38) could be suitable. Polymers like polyetheretherketone (PEEK) or polyvinyldisulfone or polyvinylidene fluoride (PVDF) can also be used.

The flow cell body can be formed from a conductive material. Alternately, the conductive materials can be physically pressed against the flow cell bodies, or they can be attached to the flow cell bodies, mechanically or chemically. As an example of mechanical bonding, a female part at the outlet port of the first flow cell body or the inlet port of the second flow cell body can be adapted to receive a male part of a conductive material, so that the two are physically mated. As an example of a chemical bonding, the conductive material can be adhered to one or both of the flow cell bodies, such as by an epoxy resin or other suitable adhesive that resists degradation under the conditions of use, namely, high pressure, organic solvents, and the like.

The flow cells are designed such that a light beam can pass through the transparent or translucent portion in a linear or substantially linear path, and travel to a photodetector. It is important that the path be linear or substantially linear, so as to minimize interference and maximize the signal reaching the detector.

In one embodiment, a tube is inserted within the flow cell. The exterior of the tube includes two (or more) spirals, and each spiral connects one of the (inlet, outlet) with the optical path of the cell. The tube imparts a vortex in the fluid passing through the flow cell. In another embodiment, the flow cells comprise angled holes or spiral-forming structures (like rifling) for this same purpose.

Flow cells comprising a tube comprising two or more spirals, or angled holes, or spiral-forming structures, such as rifiling, are a separate embodiment of the invention, and can be used without the other features of the flow-cell systems described herein.

In one embodiment, a housing supports the first optical flow cell body and the second optical flow cell body, such that the first and second optical flow cell bodies are in series, with the outlet port of the first optical flow cell body adjacent to the inlet port of the second optical flow cell body. In another embodiment, the flow cells are stackable in series, each with its own housing. An advantage to this approach is that, whereas on information and belief, currently-available detector systems have tubing connecting a UV detector to a conductivity detector, the need for such tubing is avoided using the flow cell systems described herein.

II. Light Sources and Associated Lenses/Grating/Prisms/Filters

Light from one or more suitable light sources can be passed through the window of a flow cell body, such that it travels through the flow cell and the liquid whose absorbance is to be measured and on to a photodetector. The absorbance can be computed, and where the eluent includes a protein containing one or more absorbing amino acids, the absorbance will be higher than when no protein is present.

Light can be passed from a single light source through one of the optical flow cell bodies, from multiple sources through one of the optical flow cell bodies, or from multiple sources through multiple optical flow cell bodies.

The light source(s) can be located in the housing, or can be located outside of the housing. Where the light source(s) are located outside of the housing, the light can be transmitted optionally including one or more lens elements into the housing through air, or by means of a fiber optic cable, or other fiber optic element. In this embodiment, the fiber optic element ideally resides, at least in part, within the housing.

The light source(s) must be capable of generating light at a wavelength that is suitable for the molecules being detected. Typically, this light is in the UV or visible range (UV/VIS). Where fluorescence is also being measured, at least one light source must be capable of generating light that stimulates fluorescence in the substance to be detected.

It is relatively important that the light be monochromatic light, or, where it is not monochromatic, that it be passed through a prism, holographic grating, or bandpass filter so that light of substantially only one wavelength passes through the flow cell. By "substantially only one wavelength" is meant light with wavelength intensity following a Gaussian distribution, with around 80 or more percent of the light falling within a range of around 20 nm or less from the maximum wavelength.

Where the light is monochromatic light, or nearly monochromatic light, and is of a desired wavelength for the analysis, there is no need to separate or filter the light using a prism, holographic grating or bandpass filter and direct light of a desired wavelength through the optical flow cell body. On the other hand, where the light is not monochromatic, it may be desirable to use a prism or grating or filter to select the desired wavelength or range of wavelengths of light and direct the resulting light through the optical flow cell body. When a prism, grating or filter is used, the transmitted wavelength can be varied, depending on the molecule of interest being eluted from a column and through the flow cell system. For example, light at a wavelength of 280 nm is absorbed by most amino acids and is preferred for measuring protein concentration, and 260 nm is preferred for measuring DNA concentration (see, for example, Sambrook and Russell (2001). Molecular Cloning: A Laboratory Manual (3rd ed.). Cold Spring Harbor Laboratory Press. ISBN 978-0-87969-577-4.

It can be desirable to simplify the overall flow cell system, so in one embodiment, the light is monochromatic or substantially monochromatic, and in one aspect of this embodiment, the light is monochromatic LED light.

In some embodiments, it may be desired to focus the light beams so that they pass through the flow cell window. In these embodiments, the system can include one or more lenses, filters, and/or apertures, positioned such that the lenses, filters, and/or apertures are in the path of the light emitted from one or more of the light sources, before and/or after the light passes through the first or second optical flow cell body. Representative lenses include concave, convex, plano-concave, plano-convex, ball, hemispherical, collimating, and Fresnel lenses.

Representative Light Sources

Representative light sources include, but are not limited to, lasers, light emitting diodes (LEDs), such as TOPLEDs (OSRAM Opto Semiconductor), UVTOP® (Sensor Electronic Technologies), or Nichia UV-LEDs (Nichia Corporation, Japan) some of which provide monochromatic light, or nearly monochromatic light, and deuterium, xenon, mercury, zinc, and tungsten lamps, which provide broader spectrum light output.

LEDs

A light-emitting diode (LED) is a two-lead semiconductor light source that resembles a basic pn-junction diode, except that an LED also emits light. When an LED's anode lead has a voltage that is more positive than its cathode lead by at least the LED's forward voltage drop, current flows. Electrons are able to recombine with holes within the device, releasing energy in the form of photons. This effect is called electroluminescence, and the color of the light (corresponding to the energy of the photon) is determined by the energy band gap of the semiconductor.

A single light source can include two or more LEDs, each transmitting light at a desired frequency. Where light at two more frequencies is desired, the LEDs can be offset so that they each transmit beams of light through substantially the same path through the flow cell. Although it is most preferred that light pass directly through the flow cell to the photodetector, if the beams of light are only slightly offset, they can transmit beams down substantially the same path, such that the beams are effectively coaxial. By "substantially the same path" and "effectively coaxial" is meant that the light transmission is 95% or more of the light that would travel down the path if the path were completely straight.

While not wishing to be bound to a particular theory, it is preferred to use LED lights that have a focused emission profile (i.e., which emit light with a Gaussian distribution of wavelengths centered around a desired wavelength) over using a light source that generates a broad spectrum of wavelengths that have to be passed through a filter, prism, or grating, as such can substantially simplify the flow cell systems. Moreover, LED lights are relatively small, so the footprint of the flow cell systems can be reduced by using LED lights.

UVTOP® LEDs

UVTOP® is a series of deep ultraviolet light emitting diodes with peak emission wavelengths from 240 nm to 355 nm. The LEDs are hermetically sealed in metal-glass transistor outline (TO) packages with a choice of UV-transparent optical windows and lenses for beam profiling. These lights can be preferred, as they can be custom tailored to emit light with a maximum emission at a desired wavelength.

On information and belief, these LEDs can transmit light with as narrow a wavelength distribution, or nearly so, as polychromatic light from other sources that has been passed through a prism, filter, or grating.

Use of LED Lights With Two or More Sources of Light

In one embodiment, each light source package includes more than one LED device, where each LED can be independently enabled. In this embodiment, a first light pulse from one LED can be passed through the flow cell, followed by a second light pulse through the same flow cell. Both LEDs can be of the same wavelength or different wavelengths to confirm the value of the other LED or to return additional property data on the liquid samples under measurement.

As discussed above, it is important that the light beams pass in a path substantially perpendicular to the optical bore through the flow cell. A single light emitting device package containing more than one light LED source element within it can be used, where the light sources are substantially close to each other, such that each light source reaches the window substantially co-axially. As the light source deviates from the axis through the optical bore (said axis is also substantially normal to the windows), greater percentages of the incident light are reflected away from the photodetector. For example, the individual light source elements can be offset from the flow cell optical axis by as much as 5° and still deliver sufficient light to the photodetector for measurement. The use of one conduit (in this embodiment, the optical bore) to transmit multiple wavelengths at different times is analogous to the technique known to those of skill in the art of signal transmission as time division multiplexing. In time division multiplexing, two or more signals are interleaved in time through the same channel, thereby minimizing the number of channels required. Similarly to telephone lines, additional flow cells are expensive and should be minimized.

The use of multiple wavelengths, pulsed at different times along a given cycle, is analogous to the technique known to those of skill in the art as time division multiplexing. That is, time-division multiplexing is used primarily for digital signals, but may be applied in analog multiplexing, in which two or more signals are transferred appearing simultaneously as sub-channels in one communication channel, but are physically taking turns on the channel.

The use of a light source comprising more than one LED light, with each LED transmitting light at a different wavelength, allows one to transmit light through a flow cell at more than one wavelength, using pulses of light at each desired wavelength.

The light source(s) can be located in the housing, or can be located outside of the housing. Where the light source(s) are located outside of the housing, the light can be transmitted optionally including one or more lens elements into the housing through air, or by means of a fiber optic cable, or other fiber optic element. In this embodiment, the fiber optic element ideally resides, at least in part, within the housing.

The light source(s) must be capable of generating light at a wavelength that is suitable for the molecules being detected. Typically, this light is in the UV or UV/VIS range. Where fluorescence is also being measured, at least one light source must be capable of generating light that elicits fluorescence in the substance to be detected.

Use of High Intensity Light to Minimize the Effect of Noise

Because the flow cells are relatively small and typically pass relatively small optical powers, the photodetectors used to measure the transmitted light rely on small currents, often measured in the nano Ampere scale. Where there is only a relatively small amount of energy being detected, even tiny levels of background noise cause the signal to noise ratio (S/N) to be detrimental to the measurement. In one embodiment, this effect is minimized by using light with a relatively high intensity. The relatively high light intensity provides significantly more signal to the detector, thus improving S/N. Liquid solutions passing through the flow cell can be negatively affected by high energy UV radiation, which can denature proteins and can precipitate on the flow cell surfaces, artificially increasing the measured absorbance. Accordingly, in one aspect of this embodiment, this limitation is addressed by operating the light source in a high peak power, short duration pulsed mode. Between pulses, the light system cools sufficiently such that the light source lifetime is maintained at or near normal levels and the flow cell windows are not fouled. To measure the dynamically flowing liquid sample with sufficient resolution, the light source is pulsed rapidly. For example, the pulse intervals may be between 0.1 and 500 milliseconds. Within each pulse, the light source will be on less than about 50% of the complete cycle, preferably less than about 25% of the cycle, and still more preferably, less than about 10% of the cycle. For example, one can have a 76 microsecond light pulse within a one millisecond cycle. Pulse cycles shorter than about 0.1 milliseconds become difficult to control, resulting in signal ringing and timing inaccuracies. The light pulse should not exceed around 50% of the cycle time for sufficient thermal recovery between pulses. The frequency of the pulses, and the length of the cycle, can be adjusted using appropriate hardware and software controls.

III. Photodetectors

In use, light from one or more of the suitable light sources described can be passed through the window(s) of the flow cells, such that the light travels through the flow cell(s), and the liquid whose absorbance is to be measured, and on to a photodetector. The absorbance of the light can be measured, and where the eluent includes a protein containing one or more absorbing amino acids, the absorbance will be higher than when no protein is present.

Light can be passed from a single light source through one of the optical flow cell bodies, from multiple sources through one of the optical flow cell bodies, or from multiple sources through both of the optical flow cell bodies.

The light passes on to a photodetector. The photodetector can be, for example, a quantum dot photoconductor or a photodiode, each of which can handle wavelengths in the visible and infrared spectral regions.

First Sensor Photodiodes

A photodiode is an active component that converts light into an electrical voltage (photovoltaic effect) or photocurrent. The p-n junction in the silicon semiconductor generally serves as the physical basis for this process, though a structure rather than a p-n junction can be used to increase the speed of response. When photons with sufficient energy are absorbed by the detector, this results in the formation of charge carriers (electron-hole pairs), which are separated in the space-charge region and thus generate the photocurrent.

Photodiodes may contain optical filters, built-in lenses, and may have large or small surface areas.

Minimization of Signal Noise Via Synchronous Gating with Pulsed Light

When the light is pulsed, it is also possible to minimize noise, improving the signal to noise ratio by synchronously gating the photodetector, so the amplifier accumulates signal in approximately the same time frame as the source light is active. Photodiodes and other photodetectors generate some electricity regardless of light falling on their active surfaces. This electricity is commonly known as "dark current" because the current flows even if the sensor's surface is dark. Accordingly, in one embodiment, the photodetector is pulsed to convert light intensity to an output current that mirrors the pulsing of the light source. In one aspect of this embodiment, the photodetector includes an amplifier, and the pulsing of the photodetector is accomplished by synchronously gating the amplifier.

Sample and Hold Circuit

From the Beer-Lambert law, accurate absorbance requires accurate photodiode measurements. The photodiode measuring circuit depends on precision microsecond timing to provide a highly accurate measurement. The control system includes a microcontroller. The microcontroller may be busy with another task for a few microseconds, resulting in measurement start or duration delays. This error in timing would be detrimental to the light measurement, reducing the accuracy of the absorbance measurement.

To counter this timing difficulty, the same gating signal used to enable the LED serves a second purpose; connecting the photodiode to a storage capacitor. This capacitor forms a simple, inexpensive and effective sample and hold circuit, storing the photodiode energy for later measurement. The energy remains in the capacitor until the microcontroller instructs the analog to digital converter to measure the energy by measuring the voltage across the capacitor. By using this sample and hold circuit precisely timed to the LED's enable signal and asynchronously timed to the microcontroller, the precision timing requirement for accurate absorbance is met without requiring precision timing from the microcontroller.

Figure 5:
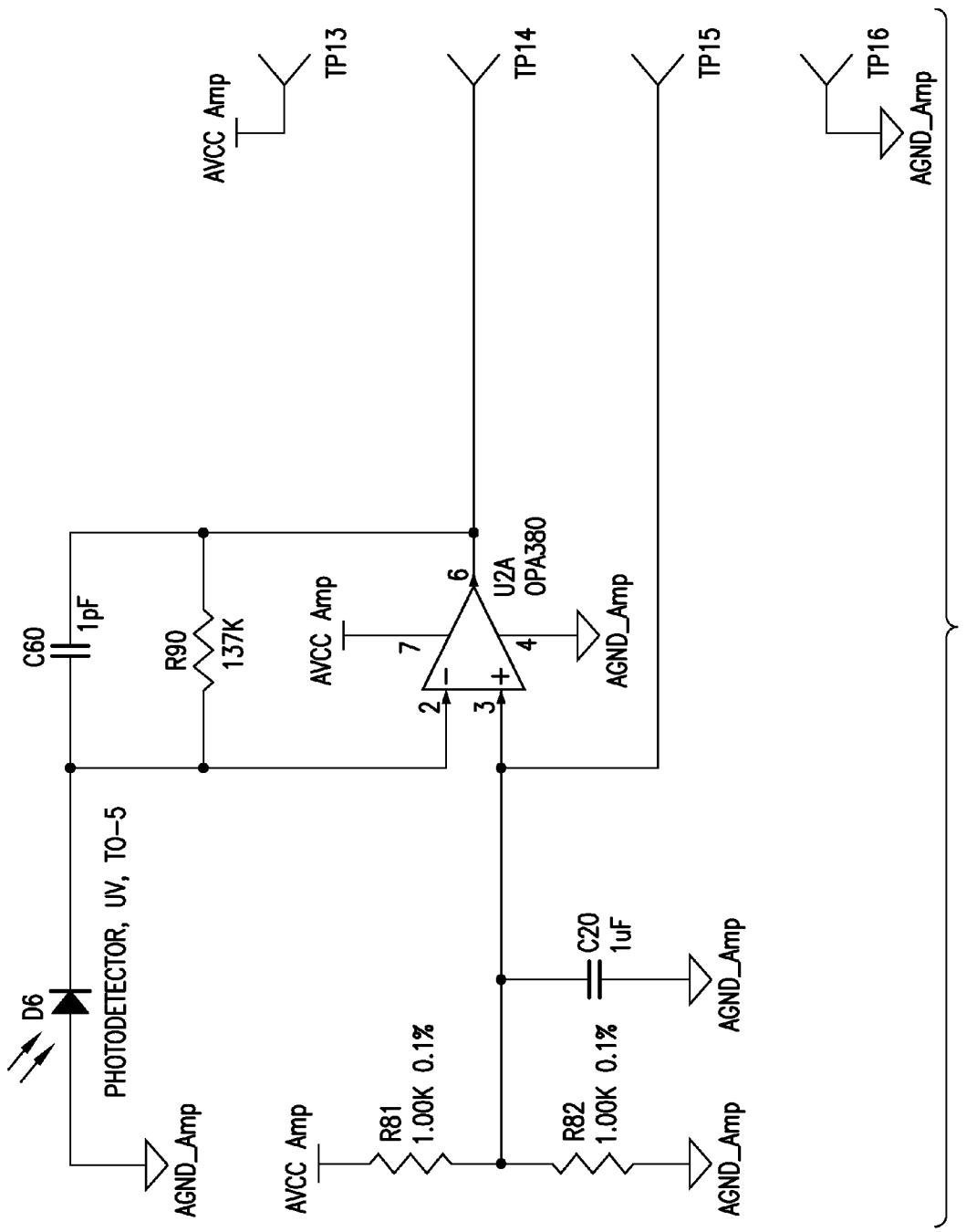
FIG. 5 shows a schematic illustration of a sample and hold circuit.

A schematic illustration of a representative circuit is shown in FIG. 5.

Controlling the Pulses of Light, and the Synchronous Gating of the Photodetector The duration of each light pulse and the duration of the complete cycle can be independently adjusted using appropriate software commands.

Pulsed Gate Control

The stream of pulses is composed of a series of digital on (high) and off (low) voltages. In one aspect of the embodiment, this series of changing voltages is generated by pulse width modulation (PWM) circuitry and instructional code (firmware and software). A pulse width modulated output series oscillates between digital on and off under supervisory control. The period of the pulse is the time between rising transitions (off to on). The width is the duration of each on transition. For example, the period of the PWM may be 1000 microseconds. The pulse width might be 76 microseconds. In this example, a LED and photodiode amplifier could be gated by the on portion of the PWM cycle, with the LED and photodiode amplifier being active for the 76 millisecond portion of the pwm and being off for the 924 millisecond portion of the PWM cycle. Alternately, the circuit can be configured to make the LED and photodiode amplifier active during the off portion of the PWM cycle and inactive during the on portion of the PWM cycle.

The PWM circuitry may be incorporated into the controlling and computing element, for example a Freescale Kinetis K20 microcontroller, an Atmel ATMEGA or ATTiny microcontroller) or the PWM circuitry can be constructed from individual logic elements.

In another embodiment, the stream of pulses may be created using a resistor-capacitor circuit (RC) or an inductor-resistor-capacitor circuit (LCR). Further embodiments could use commercially available integrated circuits constructed primarily to provide timing functions. Examples include the generic "555 timer IC" family. The LCR and R-C circuits suffer from tolerance and temperature induced inaccuracies. The 555 timer is less susceptible to these inaccuracies but is not as easily adjusted as the purpose-built PWM circuitry.

In still another embodiment, a computer processor output pin may be toggled directly by the processor's instruction code using the internal or external timing standard incorporated within the processor. Codes monitor the elapsed time and toggle the output pin between high and low at precisely the proper time. This timing and toggling can be accomplished with interrupts and interrupt service routines, whereby instructional code monitors the processor's clock and calls a subroutine whenever the processor clock reports a preprogrammed elapsed time. The subroutine instructs the processor to toggle the output pin. The subroutine may also set the next interrupt service routine to continue the toggling process indefinitely.

Use of Multiple Wavelengths of Light

In one embodiment, light is measured in each of the two flow cells at different wavelengths. For example, where the wavelengths are set at 260 nm and 280 nm, one can measure protein and DNA concentrations. In another embodiment, light is measured in each of the two flow cells at the same wavelength. This can help determine whether there are any distortions caused by artifacts in one of the flow cells, because in the absence of such artifacts, assuming the same light intensity, flow cell size, and flow cell composition, the two signals should be identical. In a third embodiment, in addition to having two light sources at the same light intensity, one in each flow cell, one can further have two (or more) light sources in one or both of the flow cells. Particularly where the light is pulsed, as described above, the system can provide pulses of light at a first wavelength in the cycle, and pulses of light at a second wavelength either within the same cycle, or in a separate cycle. It is generally preferred to allow sufficient time between pulses of light of different frequencies, so as to avoid interference by the light beams.

IV. Conductivity Measurement

The flow cell systems described herein further comprise components that enable the conductivity of the mobile phase to be measured as it passes through the flow cell.

Typically, a conductivity cell is a device that includes electrodes which sense the electrical conductivity of a substance, which, in an HPLC instrument, is the mobile phase plus any compounds of interest that have eluted through the column and are present in the mobile phase.

Common configurations include two electrode cells and four electrode conductivity cells. The main trait that differentiates each type is the conductivity cell constant (K). Electrode geometry, size, the distance between each, and the pattern of the electrical field present determine the cell constant. Generally, the constant is higher for cells with small electrodes that are spaced far apart, and is lower for cells with larger electrodes spaced closer together.

To measure conductivity, the cell constant and the conductance of the material have to be multiplied. The fringe field effect must also be factored into the equation, which is simplified by also performing a measurement of a solution in which the electrical conductivity is known. By calibrating a probe with a conductivity cell, it is possible to account for an unknown cell constant that changes as the electrode deteriorates. The reading can also be adjusted to a real value based on the ambient temperature when the measurement is taken.

In the flow cell systems described herein, a first conductive material is adjacent to the outlet port of the first optical flow cell body, positioned such that would be in contact with any fluid passing through the flow cell, a second conductive material is adjacent to the inlet port of the second optical flow cell body, positioned such that would be in contact with any fluid passing through the flow cell, and an insulator between the first and second conductive materials.

As fluid flows through the first flow cell, the insulator, and the second flow cell, conductivity can be measured. Conductivity of that specimen fluid is measured by connecting the cell bodies, or, more specifically, connecting the conductive material present on both sides of the insulator, to a power supply and applying an AC current thereto. The variation in the electrical resistance of the specimen liquid can be measured, either continuously, or at desired times during a chromatographic run. In one embodiment, the conductivity is also measured in a pulsed manner rather than in a continuous manner. In one aspect of this embodiment, the pulses by which conductivity is measured are timed to avoid overlapping with the light pulses, so that noise and other artifacts caused by the light signal, and detection thereof, are not inadvertently captured as part of the conductivity measurement or vice versa.

The conductive materials can be physically pressed against the optical flow cell bodies, or they can be attached to the optical flow cell bodies, mechanically or chemically. As an example of mechanical bonding, a female part at the outlet port of the first optical flow cell body or the inlet port of the optical second flow cell body can be adapted to receive a male part of a conductive material, so that the two are physically mated. As an example of a chemical bonding, the conductive material can be adhered to one or both of the optical flow cell bodies, such as by an epoxy resin or other suitable adhesive that resists degradation under the conditions of use, namely, high pressure, organic solvents, and the like.

The simplest conductive materials are washers, including metallic washers or washers made of or covered by conductive substances (such as conductive polymers or coatings or platings). To provide a better connection between the optical flow cell bodies and the conductive materials, the optical flow cell bodies can include wires, metal plating, and the like. In one aspect of this embodiment, a portion of the flow cell is plated with a metal, such as gold.

The conductivity measuring system can further include an alternating voltage source (AC source). The AC source is connected, directly or indirectly, to the first and second conductive materials, so as to complete a circuit. In one embodiment, the AC source is capable of alternating at more than one frequency.

The presence of the two conductive electrodes with an insulator disposed between them allows one to perform conductivity measurements when a) a liquid solution is passed through the flow cell electrodes and b) the conductive materials are connected to an AC source to drive current through the materials. The liquid solution completes the circuit between the conductive materials, and the current through the circuit changes as the concentration of proteins or other molecules of interest in the liquid solution changes.

The flow cell systems described herein comprise two or more electrodes, made from a conductive material compatible with the fluids to be measured. Often, the same materials used in the flow cell can be used (examples of which include titanium Ti 6Al-4V and similar alloys).

Ideally, the electrode is produced from a material which forms an oxide that is minimally insulating, so an oxide coating, if and when formed, does not interfere with the conductivity measurement. Platinum (Pt) and gold (Au) electrodes are minimally reactive but expensive, but the electrodes can be plated with Pt or Au to enhance conductivity.

The insulator separating the conductivity electrodes is made from an essentially non-conductive, physically rigid material compatible with the liquid to be measured. Representative insulators include fluorinated polymers, such as PTFE (DuPont Teflon®), ETFE (DuPont Tefzel®), FEP, PVDF, PES and PEEK.

A system of op-amps and switches creates an alternating current (AC) square wave to excite the conductivity electrodes. The AC reversals minimize galvanic transfer of metal from one electrode to the other.

The conducted current is measured indirectly by measuring the voltage drop across a current sense resistor. This voltage is amplified and converted to a digital signal using an analog to digital converter system.

Noise Suppression in Conductivity Measurements

Capacitive effects and fringe effects can result in erroneous readings. Both effects can be substantially subtracted using multiple techniques. In one embodiment, the conductivity measurement system comprises more than two conductive material electrodes, such as 3, 4, 5, 6, or more conductive material electrodes, which, when connected to an AC source, function as reference electrodes. In one aspect of this embodiment, where the initial electrodes are formed by the conductive materials at the outlet port of the first flow cell body and the inlet port of the second flow cell body, an additional two electrodes can be formed by placing conductive materials at the inlet port of the first flow cell body, and the outlet port of the second flow cell body. In one aspect of this embodiment, where the initial electrodes are formed by the conductive materials at the outlet port of the first optical flow cell body and the inlet port of the second optical flow cell body, an additional two electrodes can be formed by placing conductive materials at the inlet port of the first optical flow cell body, and the outlet port of the second optical flow cell body.

Additional conductivity electrodes beyond two collectively form a reference pair having the same error signal as the measuring electrode pair but do not measure the liquid conductivity. By subtracting the reference signal, only the conductivity due to liquid conductance remains, effectively subtracting the non-conductivity current effects.

In another embodiment, the AC source operates at varying frequencies depending on the measured value of conductance. By varying the AC source frequency, cell capacitive effects become apparent and separately measurable. These capacitive effects can be subtracted from the measurement to improve measurement accuracy.

The electrodes, flow cells, and insulator used to measure conductivity are just some of the components used to measure conductivity. In addition, it is also useful to provide a transmitter and controller for signal conditioning, as well as a connecting cable.

Excitation Section

A circuit creates the AC voltage delivered to the electrodes. The circuit consists of an alternating pulse train that switches from an inverting amplifier to a non-inverting amplifier. Alternately, the pulse train can switch from a low gain amplifier to a high gain amplifier, creating an alternating output. The pulse train can be created by a computer processor, a R-C or LCR network or a 555 timer, or PWM or directly from a programmed computer processor manipulating one or more output pins to create a pulse train.

Sensing Section

The voltage across the electrodes is amplified then measured by an analog to digital converter (ADC). This ADC samples the amplifier's output and transforms the measured voltage to a digital value. The resulting digital value is received by a computer processor where it is further processed into a conductivity reading.

Processing Section

The sensing section's digital representation of the measured voltage is read multiple times (between 2 and 100,000, for example) before the computer processor delivers a final value. The final value is an average of the multiple readings to smooth the effect of a few aberrant readings within a measurement cycle.

V. Optional Temperature Measurement

The measured conductance varies with the liquid's temperature. The value, which is a digital value, is typically corrected for temperature effects using the following calculations:

$$C_{25} = \frac{C_t}{1 + \alpha(t - 25)}$$

Where $C_{25}$ is the measured conductivity at 25° C., $\alpha$ is the temperature coefficient of the calibration solution in ° C. $C_t$ is the temperature at which the conductivity measurement is desired.

Because conductance, fluorescence, and the like can vary depending on the temperature of the liquid solution, it can be important to have the ability to measure the temperature. Accordingly, in some embodiments, the flow cell system, particularly the housing portion of the system, includes a temperature measuring device, such as a thermocouple or resistive temperature device (often called RTD, or Pt100), although any device.

VI. Measuring the Concentration of Biomolecules in the Eluent by UV Transmission One way to determine the concentration of biomolecules in the mobile phase as it passes through a flow cell is to measure the UV transmission of the mobile phase, and compare the transmission to a set of dilution-based standard curves, or to use an internal standard.

Modern high performance liquid chromatography (HPLC)-diode array detectors, including those with features such as multiple wavelength monitoring, are capable of maintaining a high degree of response reproducibility over extended periods of time. Because of this high degree of reproducibility, it has been suggested that detector response factors, rather than dilution based standard curves, can also be used to measure concentrations of proteins and pharmaceuticals. Eberlein, "Quantitation of proteins using HPLC-detector response rather than standard curve comparison," J Pharm Biomed Anal., September; 13(10):1263-71 (1995).

These techniques are well known, and are not discussed further herein. At least in some embodiments, the flow cell systems described herein enable one to measure UV transmission, using relatively small flow cells, and relatively simplified optics and/or electronics, that is as accurate as measurements taken using conventional flow cells with relatively larger footprints and more complicated optics and/or electronics.

VII. Fluorescence Measurements

In a fluorescence detector, a sample to be analyzed is introduced into a flow cell. The flow cell is irradiated with excitation light; light of a specific wavelength. The amount of fluorescence emitted from the excited sample is measured by a photodetector to determine the concentration or amount of each of the components of the sample. Methods of performing assays on fluorescent materials are well known in the art and are described, for example, in Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N. J., Modern Molecular Photochemistry, Menlo Park: Benjamin/Cummings Publishing Col, Inc. (1978), pp. 296-361.

In general, excitation radiation, from an excitation source having a first wavelength, passes through excitation optics. The excitation optics cause the excitation radiation to excite the sample. In response, fluorescent proteins in the sample emit radiation which has a wavelength that is different from the excitation wavelength. Collection optics then collect the emission from the sample. The device can include a temperature controller to maintain the sample at a specific temperature while it is being scanned.

VIII. Conductivity Measurements

Conductivity detection is used to detect inorganic and organic ionic species in the mobile phase. All ionic species are electrically conducting, so conductometric detection is a universal detection technique.

Conductivity, the reciprocal of electrical resistivity, is the ability of a solution to conduct electricity. Conductivity is results from the mobility of dissociated anions and cations in a solution. In low to moderate concentrations, conductivity can be predicted. In high concentrations, physical effects contribute to the electron mobility.

Conductivity is temperature dependent. Unless stated otherwise, conductivity references standard temperature (25° C.).

The use of conductivity measurements to determine the concentration of components in a mobile phase is well known, and is described, for example, in Keithley, Application Note Series, Number 2615, "Measuring the Resistivity and Determining the Conductivity Type of Semiconductor Materials Using a Four-Point Collinear Probe and the Model 6221 DC and AC Current Source," Copyright 2005, Keithley Instruments, Inc.

The following is a standardized method of creating conductive solutions:

A chloride salt like potassium chloride (KCl) or sodium chloride (NaCl) in deionized water can be used to create standardized solutions.

| Ion(s) | Molar mass $\left(\frac{g}{mol}\right)$ | Conductivity @ 25° C. $\left(\frac{\mu S \cdot L}{mol \cdot cm}\right)$ | Conductivity @ 25° C. $\left(\frac{\mu S \cdot L}{mol \cdot cm}\right)$ |
|---|---|---|---|
| K⁺ | 39.0983 | | 73.5 |
| Cl⁻ | 35.4527 | 69 | 76.35 |
| Na⁺ | 22.98977 | 45.0 | 50.1 |
| KCl | 74.551 | | |
| NaCl | | | |

Conductivity Range Calculations 200 mS/cm range with 0.01 µS maximum resolution requires a 200 ms/0.01 µs=20,000,000:1 granularity assuming a linear measurement of excitation current and voltage. Assuming a 12-bit digital-to-analog converter (DAC) controls excitation voltage, a reasonable range for this voltage is a 100:1 ratio from 5 Vp-p to 50 mVp-p. The DAC ideally controls voltage with a 20M/100=200,000 point resolution. A 20-bit DAC provides 262K:1 resolution assuming two resolution bits are wasted as noise. By increasing the low excitation voltage to 25 mVpp, and adjusting the current measurement gain, the system provides a range of 500 mS with a 0.01 uS maximum resolution.

Capacitance

The capacitance of the cell affects conductivity. The separated electrodes naturally form a capacitor, During each alternation of the excitation voltage, a charge is stored on this unintentional capacitor. This charge artificially increases the apparent conductivity. Increasing the alternation frequency as the apparent conductivity increases reduces the capacitive error because the unintentional capacitor has less time to charge to a value affecting the measurement.

The YSI 3100 laboratory conductivity instrument (YSI Incorporated, Yellow Spring, Ohio), uses the frequencies shown in the following table through the measuring range, and these frequencies can also be used in the devices described herein:

| Measuring range | Accuracy | Resolution | Excitation Frequency |
|---|---|---|---|
| 0 to 49.99 µS/cm | ±0.50% full scale | 0.01 µS/cm | 70 Hz |
| 0 to 499.9 µS/cm | ±0.50% full scale | 0.1 µS/cm | 70 Hz |
| 0 to 4999 µS/cm | ±0.50% full scale | 1 µS/cm | 240 Hz |
| 0 to 49.99 mS/cm | ±0.50% full scale | 0.01 mS/cm | 1562 Hz |
| 0 to 499.9 mS/cm | ±0.50% full scale | 0.1 mS/cm | 1562 Hz |

The manual for Radiometer Analytical SAS' CDM230 conductivity meter lists the frequencies shown in the following table, and these frequencies can also be used in the devices described herein:

| Measuring range | Accuracy | Excitation Frequency |
|---|---|---|
| 0.0001-4.000 µS | ±0.5% | 94 Hz |
| 0.01-40.00 µS | | 94 Hz |
| 0.1-400.00 µS | | 375 Hz |
| 0.001-4.000 mS | ±0.2% | 2930 Hz |
| 0.01-40.00 mS | | 23.4 kHz |
| 0.1-400.0 mS | | 46.9 kHz |
| 1-2000 mS | ±1% | 46.9 kHz |

IX. Liquid Chromatography Systems Comprising the Flow Cell Systems

In another embodiment, the invention relates to an overall liquid chromatography system that includes the flow cell systems described herein. In this embodiment, the complete liquid chromatography system typically includes one or more mobile phases, which are typically stored in one or more reservoirs, and a pump for moving the mobile phase(s). Where mobile phases are to be mixed, for example, when used in gradient elution, the system typically also includes one or more valves. The chromatography system also includes one or more chromatography columns, each of which include a suitable column packing material. Samples are injected onto the column(s) through a sample injection port. As the eluent (in this case, the mobile phase(s) passes through the end of the column, it can then pass through the flow cell systems described herein.

The eluent liquid exiting the chromatography column is evaluated in one or more measuring instruments known to those in the art as Detectors. In addition to including the windows through which light can pass, and conductive materials that can serve as electrodes when a current is applied, it is also important, for example, to be able to use information regarding the absorbance, fluorescence, or conductivity to determine when a molecule of interest has eluted from a column.

Accordingly, the flow cell systems can be connected to, or comprise, one or more detectors. Where light is being passed through the optical portion of the flow cell bodies, and determination of absorbance or fluorescence is desired, the detector is ideally a photodetector, such as a photodiode, charge-coupled device (CCD), photoelectron multiplier. In one embodiment, the photodetector is external to the housing, but light is transmitted to the detector via a fiber optic element that resides, at least in part, within the housing. Where conductivity is to be measured, the flow cell systems are ideally connected to, or comprise, a conductivity detector.

In addition to the flow cells and the detectors, the systems comprise:

an analysis flow passage for sending a mobile phase;

a sample injection portion for injecting a sample into the analysis flow passage; and an analysis column provided downstream of the sample injection portion on the analysis flow passage to separate a sample injected from the sample injection portion into individual components.

The detectors are provided downstream of the analysis column on the analysis flow passage to detect each of the components separated by the analysis column.

X. Use of the Chromatography Systems Comprising the Flow Cell Systems to Detect the Presence or Absence of a Compound of Interest In a further embodiment, the invention relates to a method for detecting the presence or absence of protein, DNA, or another molecule of interest in an eluent by measuring the conductivity of the eluent. The method involves passing a mobile phase through a liquid chromatography column comprising the flow cell systems described above. The conductivity of the mobile phase as it elutes from the column (i.e., the eluent) as it passes through the flow cell system can be determined, and this can be used to define baseline conductivity. A sample that comprises one or more molecules of interest, such as proteins or DNA, can then be injected onto the liquid chromatography column. A chromatographic separation is performed by pumping the eluent through the liquid chromatography column. Periodic or continuous measurements of the conductivity of the eluent can be taken as the eluent passes through the flow cell bodies. An increase in conductance relative to the baseline conductance is indicative of the presence of a molecule of interest in the eluent.

In a still further embodiment, the invention relates to a method for detecting the presence or absence of a protein, DNA, or other molecule of interest in an eluent, by measuring the absorbance or fluorescence of the eluent. The method involves passing a mobile phase eluent through a liquid chromatography column comprising a flow cell system as described herein, to form an eluent.

A beam of light, at a wavelength suitable for detecting the presence of the molecule of interest in the eluent, is passed through the first and/or second optical flow cell body of the flow cell system in a direction substantially perpendicular to the direction in which the eluent flows through the optical flow cell bodies. The light is then passed through the flow cell bodies to a photodetector, and an initial light intensity is measured.

A sample which includes one or more molecules of interest is then injected onto the liquid chromatography column. Chromatographic separation is performed by pumping the mobile phase through the chromatography column to form an eluent. The intensity of light passed through the flow cell optical paths and directed to a photodetector can be measured, either periodically or continuously, and the light intensity can be compared to the initial light intensity. A decrease in light intensity measured by the photodetector, relative to the initial light intensity, is indicative of a protein or other compound of interest's presence in the eluent.

XI. Use of the Chromatography Systems Comprising the Flow Cell Systems to Detect Errors in Gradient Elutions In a further embodiment, the conductivity portion of the detector system described herein can be used in a chromatography system to verify the mobile phase components have been attached to the proper fluid inlets and the control system has been configured to deliver the correct ratio of mobile phase components. Within many chromatography techniques, for example in biochromatography, one mobile phase component contains a substantially lower salt concentration than other mobile phase components. A transposition of this low salt component becomes apparent rapidly after the commencement of the chromatography process.

Accordingly, the flow cells described herein can be used in a method for verifying the mobile phase components in a chromatography system during gradient elution, wherein one of the mobile phase components is a salt solution. The method involves:

a) performing gradient elution on a chromatography column using a mobile phase comprising at least two mobile phase components, at least one of which is a salt solution, wherein each of the mobile phase components is introduced onto the chromatography column through a fluid inlet, the conductivity of the mobile phase varies with the concentration of the salt solution in the mobile phase in a repeatable and predictable manner, and the salt concentration of the mobile phase is adjusted based on a pre-determined schedule, using a control system configured to deliver the correct ratio of the mobile phase components, b) measuring the conductivity of the mobile phase during the gradient elution at predetermined time intervals, c) correlating the measured conductivity to a salt concentration, and d) verifying that, at a given time interval, the salt concentration is consistent with what would be expected during the gradient elution during the given time interval, wherein a salt concentration that is too low or too high is indicative that the gradient elution is not being performed according to the predetermined schedule, and wherein the conductivity is measured using a flow cell as described herein.

If the conductivity measurement indicates that the gradient elution is not being performed according to the predetermined schedule, the user performing the gradient elution can verify that the mobile phase components have been attached to the proper fluid inlets, and/or that the control system has been configured to deliver the correct ratio of mobile phase components.

The conductivity can be measured using a flow cell as described herein. However, in one aspect of this embodiment, the method can be performed on any chromatography system that includes a conductivity detector.

XII. Use of the Chromatography Systems Comprising the Flow Cell Systems to Detect the Endpoint of Chromatographic Steps In a further embodiment, the conductivity portion of the detector, the absorbance portion of the detector or both the conductivity portion and the absorbance portion in concert can be used to determine the completion of a chromatographic step. Certain steps such as equilibration, sample load, wash and regenerate are considered complete when the passage of additional mobile phase through the system results in effectively no additional chromatographic change. The chromatographic change tends to correlate with changes in absorbance, conductivity or both absorbance and conductivity. Monitoring absorbance and conductivity during these steps and further monitoring the rate of change of these parameters therefore indicates completion of the step.

Accordingly, the flow cells described herein can be used in a method for determining whether a chromatographic step has been completed. Representative steps to be analyzed for completeness include equilibration, sample loading, column washing, and column regeneration. The method involves:

a) equilibrating a chromatography column, loading a sample onto a chromtographic column, washing a chromatographic column, or regenerating a chromatographic column, b) during the equilibrating, loading, washing, or renegerating step, periodically measuring the absorbance and/or conductivity of the mobile phase eluting from the column at predetermined time intervals, c) adding mobile phase until there is effectively no change in the absorbance and/or conductivity during two predetermined time intervals, wherein, when effectively no change in the absorbance and/or conductivity is observed during two predetermined time intervals, the equilibrating, loading, washing, or renegerating step is determined to be complete.

The conductivity and/or absorbance can be measured using a flow cell as described herein. However, in one aspect of this embodiment, the method can be performed on any chromatography system including a conductivity and/or absorbance detector.

XIII. Representative Embodiment

The instant detector assembly is designed so that two optical flow cell bodies are employed as electrodes for conductivity. FIG. 1 shows one example of a flow cell assembly as described herein, which includes two flow cells within a non-conductive housing (40). Fluid flows into a first flow cell through a fluid inlet port (10). Each flow cell body (30), which acts as a conductivity detector, is held in place in the housing (40) using retaining rings (20). Light passes into each flow cell body (30) through a quartz window (50), which window is held in place using a window retainer (60). The light passes through the windows through pre-determined optical paths (70). Between each flow cell is a pair of conductive washers (80), with a non-conductive ledge (90) between the washers. Also between each flow cell is a conductivity insulator (100), ensuring that conductivity only occurs at the washers. A shielded wire (110) is attached to the washers. As fluid flows through the flow cell assembly, conductivity and UV absorption can be measured, and then the fluid exits through the fluid outlet port (120).

Figure 2:
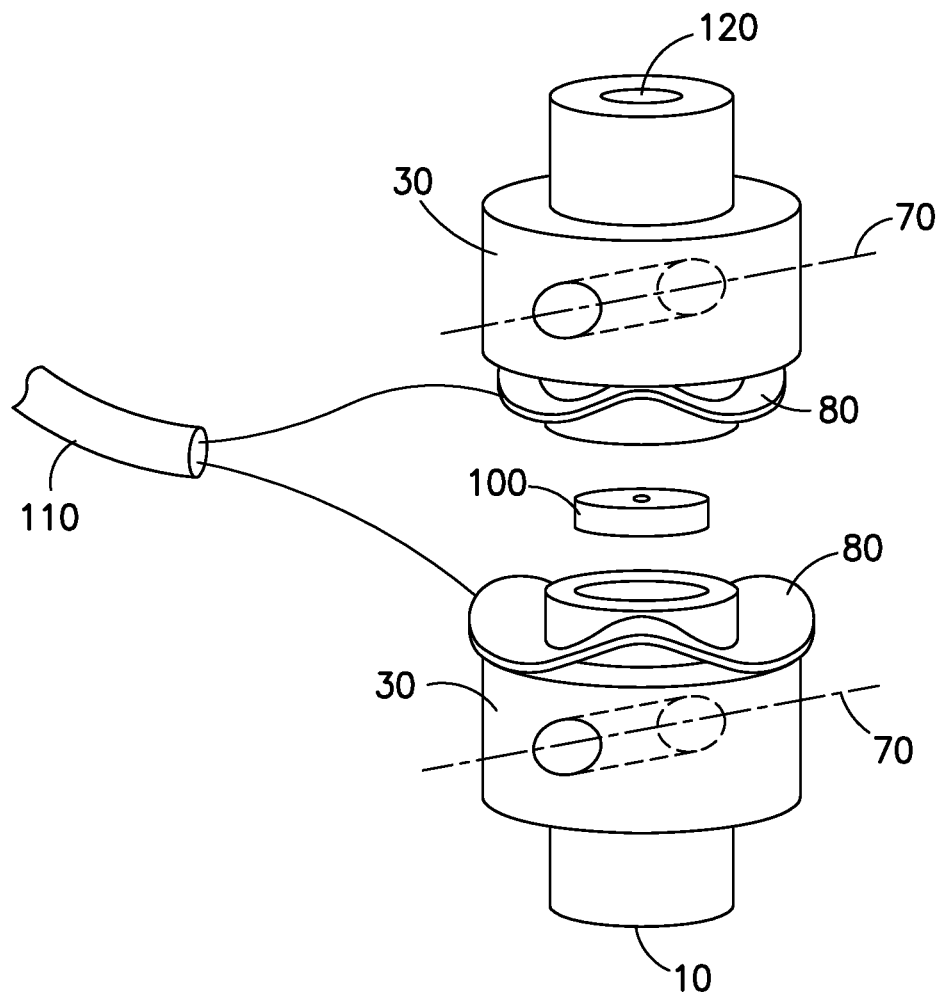
FIG. 2 shows an exploded view of an embodiment of the multi-measurement flow cell assembly.

FIG. 2 is an exploded view of a flow cell assembly without a housing, showing two flow cell bodies (30), functioning as conductivity electrodes, each with an optical path (70) through which light can pass, one with a fluid inlet port (10), and the other with a fluid outlet port (120). A conductive washer (80) is attached to each flow cell body (30), and a conductivity insulator (100) is present between the two flow cell bodies (30). A shielded wire 110 is connected to the two washers (80).

Figure 3:
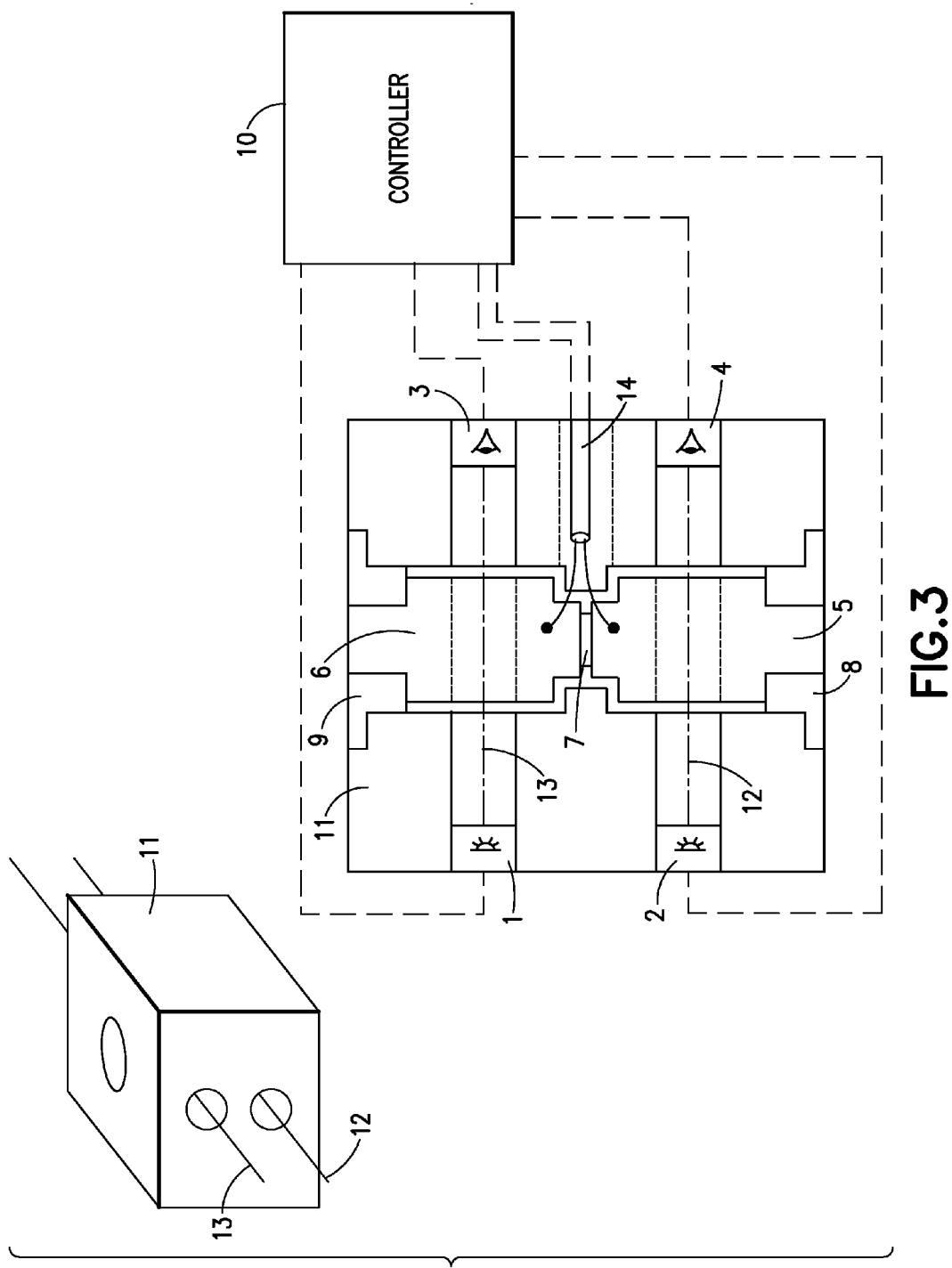
FIG. 3 shows an embodiment of a detector system including a multi-measurement flow cell assembly.

FIG. 3 is a view of the flow cell assembly showing light passing through the flow cell bodies onto photodiodes, and showing a controller for the flow cell assembly.

Two flow cell bodies (5) and (6) are secured in a housing (11) using flow cell stack nuts (8) and (9). Light from LED emitters (1) and (2) flows through the two flow cell bodies (5) and (6) through optical axes (12) and (13). After the light flows through the flow cell bodies, it impinges on photodiodes (3) and (4). The two flow cell bodies (5) and (6) are separated by a conductivity insulator (7), and connected by a shielded wire. Conductance is measured as solutions pass through the flow cells. The measurement of conductivity and UV absorbance is controlled by a controller (10).

FIG. 6 is an internal view of the embodiment shown in FIG. 3. The flow cell stack nuts (8) and (9) hold together the two flow cell bodies (5) and (6), and a conductivity insulator (7) between the two flow cell bodies. The two flow cell bodies each include a window (50) through which UV light can be transmitted.

As seen in FIGS. 1 and 3, one embodiment of the flow cell assembly includes two flow cells pressed together in a single housing with an insulator, such as a fluoropolymer disc, between them. Thereby, each flow cell acts as an electrode on either side of the insulator because the insulator prevents electrical conduction between the cell bodies other than through the liquid specimen. The detector assembly provides a continuous path, or hollow bore, whereby a specimen fluid travels directly through two consecutively aligned flow cells. As fluid flows through the first flow cell, the insulator, and the second flow cell, conductivity can be measured. Conductivity of that specimen fluid is measured by connecting the cell bodies to a power supply and applying an AC current thereto such that the variation in electrical resistance of the specimen liquid can be measured.

The detector assembly of the present invention also allows for the absorption of two different wavelengths to be measured, one in each optical flow cell body. As depicted in FIGS. 2 and 3, each optical flow cell body provides an optical path that allows light to travel from a light emitter positioned on one side of the flow cell to a detector positioned on the opposite side of the optical flow cell body. Preferably, the optical path runs through the center of the flow cell and perpendicular to its length. Returning to FIG. 1, windows may be secured into pockets on either side of the optical path and held in place by, for example, press fit aluminum rings. Preferably, the light emitters on each of the optical flow cell bodies are configured to emit different wavelengths of light enabling the device to detect the presence of two different materials. For example, one emitter may be configured to emit 260 nanometer wavelength light to detect DNA while the other emits 280 nanometer wavelength light to detect proteins.

Each of the two flow cells has a fluid inlet port on one end and an outlet port at the opposing end. Preferably, the flow cells are aligned in series, such that the outlet end of the first flow cell aligns with the inlet end of the second flow cell. This creates a single fluid path through both flow cells with a fluid port on both ends of the assembly, i.e. a detector inlet and outlet. As demonstrated in FIGS. 1 and 3, the first and second optical flow cell bodies may be secured together by a detector housing. Additionally, the light emitters and detectors may also be secured to or by the detector housing. The detector housing is preferably made of a material that absorbs light so that ambient light does not additively interfere with the transmitted light. Also, a material that is non-conductive, which isolates the flow cells and enables them to act as electrodes for conductivity measurement. By way of example, the detector housing may be comprised of acetal, such as Delrin made by DuPont.

The optical flow cell bodies may be secured to the detector housing using numerous means or materials. For example, the two flow cells and insulator may be compressed together in the detector housing using two retaining rings, one placed at the inlet end of the first optical flow cell body, and the other placed at the outlet end of the second optical flow cell body. As shown in FIG. 1, the retaining rings may be threaded and may screw into the interior edge of the detector housing. Alternatively, the retaining rings can be bolted or glued, or fastened to the detector housing using other fastening means known in the art. In still another embodiment not depicted in the figures, each optical flow cell body can have a lip or a flange designed to be bolted or otherwise fastened to the detector housing, thereby eliminating the retaining ring all together.

In the center of the detector housing, there may be a ledge that extends into the interior cavity of the housing designed to receive or support the interior portions of each of the optical flow cell bodies. As seen in FIGS. 1 and 3, the optical flow cell bodies may be formed to have a shoulder that abuts the ledge in the detector housing. Specifically, in one embodiment the first optical flow cell body has a shoulder near its outlet port while the second optical flow cell body has a shoulder near its inlet port such that the optical flow cell bodies can be inserted into the detector housing and be compressed against the ledge, or towards the ledge against the insulator separating the two optical flow cell bodies.

The optical flow cell bodies are adapted to be electrodes for measuring the conductivity of the liquid. Each of the optical flow cell bodies are connected, e.g. via a conductive wire, to a conductivity analyzer. The conductivity analyzer may be part of the controller for the detection system. As demonstrated in FIG. 3, the controller may manage the light emission and detection devices in both the first and second optical flow cell bodies, as well as the conductivity measurement system.

The flow cells also have a conductivity measurement location where the flow cell attaches to the conductivity analyzer circuit. Detection and measurement of the current passing through the liquid from one optical flow cell body to the other may be detected in any number of ways. In one embodiment, the outlet end of the first optical flow cell body and the inlet end of the second optical flow cell body are each fitted with a conductive washer. In the embodiment shown in FIGS. 1 and 2, the optical flow cell bodies are in contact with conductive wave washers soldered to Wires. Specifically, a conductive wave washer is positioned against each flow cell between the shoulder of the flow cell and the ledge of the detector housing. The wave washer is comprised of conductive material, such as copper or gold-plated copper, which contacts the flow cell housing and allows the conductivity reading between the cells to be measured. The wave washer does not necessarily contact the flow cell body around its entire circumference, and may only contact the optical flow cell body in one location or a few locations.

The wave washer provides the benefit of having a variable width that can fill the space between the detector housing and the shoulder of the flow cell, allowing for added tolerance in the detector assembly and allowing the system to fit tightly and easily together. In alternative embodiments, the conductive washer may be a standard, flat washer. In still other embodiments, the assembly may not include a washer at all, and the contact point for conductivity measurement can be a node, hook, clamp, or other contact means by which current can travel between the flow cell bodies and wires or probes leading to the conductivity analyzer circuit. As another example, the contact point can be a conductive ring, node, or disk embedded at a point in the detector housing that comes in contact with the respective flow cell body.

Figure 4:
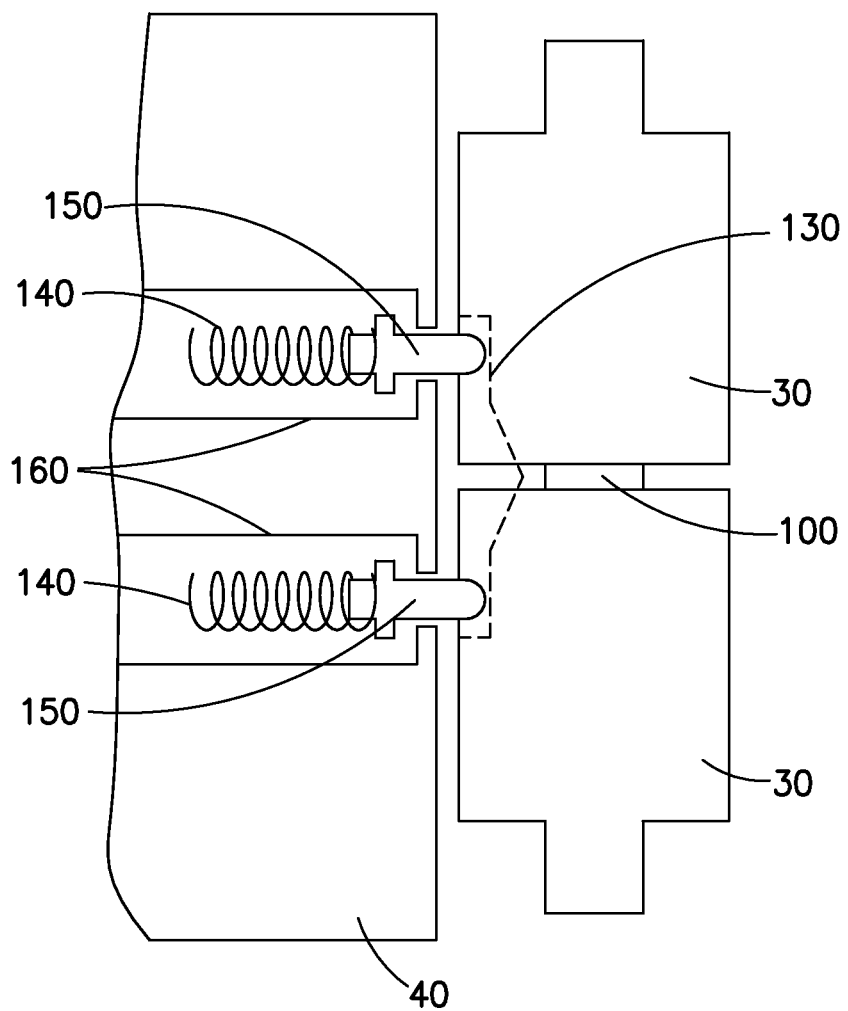
FIG. 4 shows another embodiment of a multi-measurement flow cell assembly.

In yet another alternative embodiment, the detector housing may be fitted with a pin and spring assembly that provides a conductive contact with one or more of the flow cell bodies. In the embodiment depicted in FIG. 4, the flow cell assembly includes two spring (140) and pin (150) assemblies, one for each optical flow cell body (30). The spring and pin assemblies are fitted into two bores (160), in the side of the detector housing (40), one aligned with each flow cell. However, it is also contemplated that the spring and pin assemblies can alternatively reside in slots or holes in the side of the detector housing (130), or can be fastened to the detector housing by other means. The detector housing supports each spring and pin assembly, while also permitting the assemblies to move or slide within the housing as required for the pin to make contact with and accommodate the optical flow cell bodies. Specifically, when each flow cell is inserted into the housing during assembly, the pins come in contact with the outer edge of the optical flow cell bodies. The optical flow cell body exerts force against the pin, compressing the spring, which is permitted to move within the detector housing. Thus, the pin is allowed to adjust to optical flow cell bodies of varying widths, which allows for tolerance within the assembly. As depicted in FIG. 4, the pins (150) may slide in slots or grooves (130) in the optical flow cell bodies (30). For example, the slots or grooves (130) may be shaped to engage the pin (150) in its fully extended position, and to compress the pin (150) as the optical flow cell body (30) is inserted into the housing (40).

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A flow cell system comprising:
    a) a first optical flow cell body comprising an inlet port, an outlet port, and a channel through the optical flow cell body connecting the inlet port to the outlet port,
    b) a second optical flow cell body comprising an inlet port, an outlet port, and a channel through the optical flow cell body connecting the inlet port to the outlet port,
    c) a housing which supports the first optical flow cell body and the second optical flow cell body, such that the first and second optical flow cell bodies are in series, with the outlet port of the first optical flow cell body adjacent to the inlet port of the second optical flow cell body,
    d) a first conductive material adjacent to the outlet port of the first optical flow cell body, positioned such that would be in contact with any fluid passing through the flow cell,
    e) a second conductive material adjacent to the inlet port of the second optical flow cell body, positioned such that would be in contact with any fluid passing through the flow cell, and
    f) an insulator between the first and second conductive materials.

2. The flow cell system of claim 1, wherein the first and second optical flow cell bodies comprise one or more paths through which light can pass, in a direction perpendicular to the channel between the inlet and outlet ports on the flow cell bodies.

3. The flow cell system of claim 2, wherein the path through which light can pass through the first and second optical flow cell bodies comprises a window, with an inside and an outside surface, formed of a material that a) transmits light at the frequency being evaluated, and b) has suitable physical and chemical properties to withstand the conditions of use.

4. The flow cell system of claim 3, wherein the window comprises quartz or fused silica.

5. The flow cell system of claim 3, wherein the window is coated on one or both surfaces with an anti-reflective coating.

6. The flow cell system of claim 1, wherein the system further comprises a first light source located in the housing such that it can transmit light through the path in the first optical flow cell body, a second light source located in the housing such that it can transmit light through the path in the second optical flow cell body, or a combination thereof.

7. The flow cell system of claim 6, further comprising a prism or grating, and wherein at least one of the first and second light sources emits light at more than one wavelength, and wherein the light emitted from said at least one light source is passed through said prism or grating before or after the light is passed through the flow cell.

8. The flow cell system of claim 6, wherein at least one of the first and second light sources emits light at substantially one frequency.

9. The flow cell system of claim 8, wherein the light source is an LED light.

10. The flow cell system of claim 6, wherein the first and second conductive materials are metallic washers.

11. The flow cell system of claim 1, wherein the flow cell comprises wires, metal plating, to enhance the connection of the conductive materials to the flow cell.

12. The flow cell system of claim 11, wherein a portion of the flow cell is gold plated.

13. The flow cell system of claim 1, further comprising a source of AC power, wherein the source of AC power is connected, directly or indirectly, to the first and second conductive materials so as to complete a circuit.

14. The flow cell system of claim 1, wherein the housing further comprises a detector.

15. The flow cell system of claim 14, wherein the detector is a conductivity detector.

16. The flow cell system of claim 1, wherein the housing further comprises a temperature measuring device.

17. A liquid chromatography system, comprising:
a) one or more mobile phases,
b) a pump and, optionally, a valve,
c) a chromatography column comprising a column packing material,
d) a sample injection port, and
e) a flow cell system of claim 1.

18. A method for detecting the presence or absence of a molecule of interest in an eluent, comprising:
a) passing a mobile phase through a liquid chromatography column comprising the flow cell system of claim 1, forming an eluent as the mobile phase elutes from the column,
measuring the conductivity of the eluent as it passes through the flow cell system to define a baseline conductivity,
injecting a sample which comprises one or more molecules of interest onto the liquid chromatography column,
performing a chromatographic separation by pumping the eluent through the liquid chromatography column, and
taking periodic or continuous measurements of the conductivity of the eluent as it passes through the optical flow cell bodies,
wherein an increase in conductance relative to the baseline conductance is indicative of the presence of a molecule of interest in the eluent.

19. A method for transmitting LED light through a flow cell of claim 1 and on to a photodetector, comprising pulsing one or more beams of LED light through the flow cell and on to a photodetector, where the pulses occur with cycle times between 0.1 and 500 milliseconds, and with light pulses occurring over less than about 50% of the cycle.

20. The method of claim 19, wherein the duration of the cycles and the duration of the light pulses is controlled using software.

21. The method of claim 19, wherein the photodetector is synchronously gated with the pulses of light.

22. A method for detecting the presence or absence of a molecule of interest in an eluent, comprising:
a) passing a mobile phase through a liquid chromatography column comprising the flow cell systems of claim 1,
b) determining the conductivity of the mobile phase as it elutes from the column, so as to define a baseline conductivity,
c) injecting a sample that comprises one or more molecules of interest onto the liquid chromatography column,
d) performing a chromatographic separation by pumping the eluent through the liquid chromatography column, and
e) taking periodic or continuous measurements of the conductivity of the eluent as the eluent passes through the optical flow cell bodies,
wherein an increase in conductance relative to the baseline conductance is indicative of the presence of a molecule of interest in the eluent.

23. A method for detecting the presence or absence of molecule of interest in an eluent, comprising:
a) passing a mobile phase through a liquid chromatography column comprising the flow cell systems of claim 1, forming an eluent as the mobile phase elutes from the column,
b) injecting a sample that comprises one or more molecules of interest onto the liquid chromatography column,
c) passing a beam of light, at a wavelength suitable for detecting the presence of the molecule of interest in the eluent, through the first and/or second optical flow cell body of the flow cell system in a direction substantially perpendicular to the direction in which the eluent flows through the optical flow cell bodies, and on to a photodetector, and measuring an initial light intensity,
d) performing a chromatographic separation by pumping the eluent through the liquid chromatography column,
e) passing a beam of light, either periodically or continuously, at a wavelength suitable for detecting the presence of the molecule of interest in the eluent, through the first and/or second optical flow cell body of the flow cell system in a direction substantially perpendicular to the direction in which the eluent flows through the optical flow cell bodies, and on to a photodetector, and measuring a subsequent light intensity and
f) comparing the subsequent light intensity to the initial light intensity,
wherein a decrease in light intensity measured by the photodetector, relative to the initial light intensity, is indicative of the presence of a molecule of interest in the eluent, and
wherein the absence of a decrease in light intensity measured by the photodetector, relative to the initial light intensity, is indicative of the absence of a molecule of interest in the eluent.

24. A method for verifying the mobile phase components in an HPLC during gradient elution, wherein one of the mobile phase components is a salt solution, comprising:
a) performing gradient elution on an HPLC column using a mobile phase comprising at least two mobile phase components, at least one of which is a salt solution, wherein each of the mobile phase components is introduced onto the HPLC column through a fluid inlet, the conductivity of the mobile phase varies with the concentration of the salt solution in the mobile phase in a repeatable and predictable manner, and the salt concentration of the mobile phase is adjusted based on a predetermined schedule, using a control system configured to deliver the correct ratio of the mobile phase components, b) measuring the conductivity of the mobile phase during the gradient elution at predetermined time intervals, c) correlating the measured conductivity to a salt concentration, and d) verifying that, at a given time interval, the salt concentration is consistent with what would be expected during the gradient elution during the given time interval, wherein a salt concentration that is too low or too high is indicative that the gradient elution is not being performed according to the predetermined schedule, and wherein the conductivity is measured using a flow cell of claim 1.

25. A method for determining whether a step in an HPLC chromatography has been completed, wherein the steps to be analyzed for completeness are selected from the group consisting of equilibration, sample loading, column washing, and column regeneration, comprising:

a) equilibrating an HPLC column, loading a sample onto an HPLC column, washing an HPLC column, or regenerating an HPLC column, b) during the equilibrating, loading, washing, or renegerating step, periodically measuring the absorbance and/or conductivity of the mobile phase eluting from the column at predetermined time intervals, c) adding mobile phase until there is effectively no change in the absorbance and/or conductivity during two predetermined time intervals, wherein, when effectively no change in the absorbance and/or conductivity is observed during two predetermined time intervals, the equilibrating, loading, washing, or renegerating step is determined to be complete, and wherein the conductivity and/or absorbance is measured using a flow cell of claim 1.

* * * * *